United States Patent [19]

Okazaki et al.

[11] Patent Number: 5,212,322
[45] Date of Patent: May 18, 1993

[54] MACROLIDE COMPOUNDS, THEIR PREPARATION AND THEIR USE

[75] Inventors: Takao Okazaki; Shuji Takahashi; Seigo Iwado, all of Tokyo; Keiji Tanaka, Shiga; Toshiaki Yanai, Shiga; Hisaki Kajino, Shiga, all of Japan

[73] Assignee: Sankyo Company, Limited, Tokyo, Japan

[21] Appl. No.: 644,100

[22] Filed: Jan. 22, 1991

Related U.S. Application Data

[62] Division of Ser. No. 131,413, Dec. 10, 1987, Pat. No. 5,008,191.

[30] Foreign Application Priority Data

Dec. 11, 1986 [JP]  Japan ................. 61-295452

[51] Int. Cl.⁵ ................. C07D 305/14; A01N 43/02
[52] U.S. Cl. ................. 549/265; 514/450; 424/DIG. 8
[58] Field of Search ............ 549/265; 514/450; 424/DIG. 8

[56] References Cited

U.S. PATENT DOCUMENTS

| | | | |
|---|---|---|---|
| 3,984,564 | 10/1976 | Aoki et al. | 514/423 |
| 4,378,353 | 3/1983 | Gorgelman et al. | 435/76 |
| 4,412,991 | 11/1983 | Ormond | 435/76 |
| 4,415,669 | 11/1983 | Hernandez | 435/253.5 |
| 4,429,042 | 1/1984 | Albers-Schonberg et al. | 435/253.5 |
| 4,547,491 | 10/1985 | Mrozik et al. | 549/265 |
| 4,582,852 | 4/1986 | Gehret | 549/265 |
| 4,696,945 | 9/1987 | Frei et al. | 549/265 |

FOREIGN PATENT DOCUMENTS

| | | | |
|---|---|---|---|
| 0073660 | 3/1983 | European Pat. Off. | 435/76 |
| 0074758 | 3/1983 | European Pat. Off. | |
| 0204421 | 12/1986 | European Pat. Off. | |
| 0237340 | 4/1987 | European Pat. Off. | 435/124 |
| 0237341 | 9/1987 | European Pat. Off. | |
| 0241147 | 10/1987 | European Pat. Off. | 435/124 |
| 0254583 | 1/1988 | European Pat. Off. | 435/76 |
| 0274871 | 7/1988 | European Pat. Off. | 435/76 |
| 0277916 | 8/1988 | European Pat. Off. | 435/124 |
| 64-29378 | 1/1989 | Japan . | |
| 1-197488 | 8/1989 | Japan . | |
| 1-272587 | 10/1989 | Japan . | |

OTHER PUBLICATIONS

Ono et al, Chemical Abstracts, 99, 50176 b (1983).
Ono et al, Chemical Abstracts, 99, 154946 u (1983).
R. Morrison & R. Boyd, Organic Chemistry 5th ed. Allyn and Bacon, Inc., Boston, p. 830.

Primary Examiner—John W. Rollins
Attorney, Agent, or Firm—Frishauf, Holtz, Goodman & Woodward

[57] ABSTRACT

Compounds with acaricidal, insecticidal and anthelmintic activities have the formula:

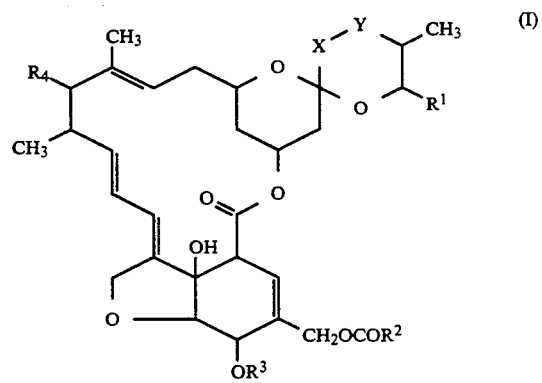

wherein:

—X—Y— is selected from the group consisting of —$CH_2$—$CH_2$—, —$CH_2$—CHOH—, —CH=CH—, and —$CH_2$—C(=O)—;

$R^1$ is selected from the group consisting of a methyl group, an ethyl group, an isopropyl group, a sec-butyl group and groups of formula —C($CH_3$)=$CHR^5$ in which $R^5$ is selected from the group consisting of a methyl group, an ethyl group and an isopropyl group;

$R^2$ represents a group of formula —($CH_2$)$_n$—C($R^6$)=C($R^7$)($R^8$) in which n is 0, 1 or 2, $R^6$ and $R^7$ each is selected from the group consisting of a hydrogen atom and a methyl group and $R^8$ is selected from the group consisting of a hydrogen atom, a $C_{1-4}$ alkyl group, a phenyl group and a phenyl group substituted with at least one substituent selected from the group consisting of halogen, methyl and nitro substituents;

$R^3$ is selected from the group consisting of a hydrogen atom, a methyl group, a hydroxy-protecting group, an ester-forming carboxylic acid residue, and an ester-forming carbonic acid residue; and $R^4$ is selected from the group consisting of a hydrogen atom and an α-L-oleandrosyl-α-L-oleandrosyloxy group, with the proviso that $R^4$ represents a hydrogen atom when the group $R^1$ is selected from the group consisting of a methyl group, an ethyl group, and groups of formula —C($CH_3$)=$CHR^5$ in which $R^5$ is selected from the group consisting of a methyl group, an ethyl group and an isopropyl group.

16 Claims, No Drawings

MACROLIDE COMPOUNDS, THEIR PREPARATION AND THEIR USE

This is a division of application Ser. No. 07/131,413 filed Dec. 10, 1987, which issued as U.S. Pat. No. 5,008,191 on Apr. 16, 1991.

BACKGROUND OF THE INVENTION

The present invention is concerned with a series of new macrolide compounds. The new compounds have valuable acaricidal, insecticidal and anthelmintic activities which are generally referred to herein as parasiticidal activities. This invention also provides methods of preparing the novel macrolide compounds and parasiticidal compositions containing the compounds, and methods for using them.

The new compounds provided by this invention are macrolides chemically related to the known milbemycins, avermectins, and similar compounds. There are several classes of known compounds with a structure based on a 16-membered macrolide ring. They are obtained by fermentation of various microorganisms or semi-synthetically by chemical derivatization of such natural fermentation products, and exhibit acaricidal, insecticidal, anthelmintic and other antiparasitic activities. The milbemycins and avermectins are examples of two such classes of known compounds, but various other classes also exist and are identified by different names or code numbers. The names for these various macrolide compounds have generally been taken from the names or code numbers of the micro-organisms which produce the naturally occurring members of each class, and these names have then been extended to cover the chemical derivatives of the same class, with the result that there has been no standardized systematic nomenclature for general use with such compounds.

In order to avoid confusion, reference in this patent specification will be made to names based on the hypothetical parent compound represented by formula (A):

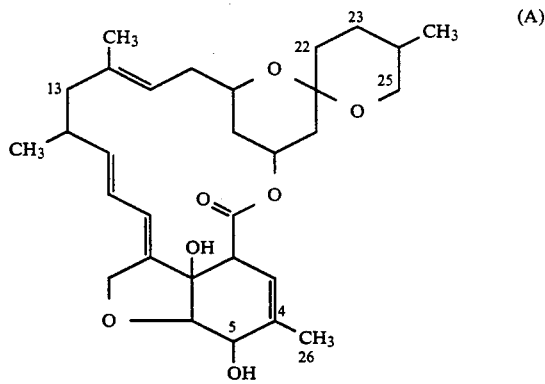

(A)

For the avoidance of doubt, formula (A) also shows the numbering of some carbon atoms most relevant to the compounds of the present invention. The methyl group at the 4-position has been numbered C-26.

The naturally produced milbemycins form a series of compounds. Milbemycins $A_3$ and $A_4$, among others, were disclosed in U.S. Pat. No. 3,950,360, and milbemycin D was disclosed in U.S. Pat. No. 4,346,171, where it was referred to as "Compound B-41D". These compounds may be represented by the above formula (A) in which position 25 is substituted respectively with a methyl group, an ethyl group or an isopropyl group.

The milbemycin analogue substituted at position 25 with a sec-butyl was disclosed in U.S. Pat. No. 4,173,571.

Various derivatives of the original milbemycins have been prepared and their activities have been investigated. For example, 5-esterified milbemycins have been disclosed in U.S. Pat. Nos. 4,201,861, 4,206,205, 4,173,571, 4,171,314, 4,203,976, 4,289,760, 4,457,920, 4,579,864 and 4,547,491; in European Patent Specifications 8184, 102,721, 115,930, 142,969, 180,539 and 184,989; and in Japanese Patent Applications Kokai 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and European Patent Specification 203,832. British Patent Specification 2,168,345 disclosed milbemycin derivatives having a carboxy or esterified carboxy substituent at position 13 in combination with a hydroxy or esterified hydroxy substituent at position 5.

Like the milbemycins, the avermectins are based upon the same 16-membered macrolide ring compound. The avermectins were disclosed, for example in J Antimicrob Agents Chemother, 1979, 15, 361 (1979) and J Am Chem Soc, 1981, 103, 4216. These compounds may be represented by the above formula (A) but with position 13 substituted with a 4'-(α-L-oleandrosyl)-α-L-oleandrosyloxy group. Position 25 may be substituted with an isopropyl group or a sec-butyl group, and either there is a carbon-carbon double bond between positions 22 and 23, or there is a hydroxy group at position 23.

The avermectins are defined as follows:

| avermectin | $C_{22}$–$C_{23}$ | $R_{25}$ | $R_{23}$ | $R_5$ |
|---|---|---|---|---|
| $A_1a$ | db | sec-Bu | H | OMe |
| $A_1b$ | db | i-Pr | H | OMe |
| $A_2a$ | sb | sec-Bu | OH | OMe |
| $A_2b$ | sb | i-Pr | OH | OMe |
| $B_1a$ | db | sec-Bu | H | OH |
| $B_1b$ | db | i-Pr | H | OH |
| $B_2a$ | sb | sec-Bu | OH | OH |
| $B_2b$ | sb | i-Pr | OH | OH |

In the above table, $R_{25}$ is a substituent at the 25 position; $R_{23}$ is a substituent at the 23 position; and $R_5$ is a substituent at the 5 position; "db" indicates a double bond between positions 22 and 23; and "sb" indicates a single bond between positions 22 and 23.

The 23-keto derivatives of avermectin $A_2a$, $A_2b$, $B_2a$ and $B_2b$ are known from U.S. Pat. No. 4,289,760. 22,23-Dihydroavermectins may be obtained by reduction of the double bond between the 22 and 23 positions and were disclosed in U.S. Pat. No. 4,199,569. The aglyclone derivatives of the avermectins, which are milbemycin analogues, have sometimes been referred to in the literature as C-076 compounds, and various derivatives are known. For example, U.S. Pat. No. 4,201,861 disclosed such derivatives substituted with a lower alkanoyl group at position 13.

European Patent Specification 74,758 disclosed avermectin compounds which are derivatized at the 4-methyl group. The conversion of the 4-methyl group to a hydroxymethyl group is described, along with the formation of various oxymethyl derivatives such as acetyloxymethyl, benzoyloxymethyl and other carbonyloxymethyl compounds.

European Patent Specification 170,006 disclosed a family of bioactive compounds produced by fermentation, identified collectively by the code number LL-F28249. Some of these have a 16-membered macrolide structure corresponding to the above formula (A), substituted with hydroxy at position 23 and with a 1-methyl-1-propenyl, 1-methyl-1-butenyl or 1,3-dimethyl-1-butenyl at position 25. In these compounds, the hydroxy at position 5 may also be replaced by methoxy.

The same or similar compounds identified as S-541 compounds are known from British Patent Specification 2,166,436. The 23-keto derivatives and 23-deoxy derivatives of S-541 are known from Belgian Patent 904,709. S-541 derivitives with a carbon-carbon double bond at positions 22 and 23 were disclosed in European Patent Specification 215,654. The 26-hydroxy and 26-$C_{1-4}$ alkanoyloxy derivatives of S-541 and of the 23-keto and 23-deoxy derivatives of S-541 are known from European Patent Specification 237,341.

British Patent Specification 2,176,182 disclosed another group of macrolide antibiotics corresponding to the above formula (A), with a hydroxy or substituted hydroxy group at position 5, a hydroxy, substituted hydroxy or keto group at position 23, and an α-branched alkenyl group at position 25.

A yet further group of related macrolide derivatives was disclosed in Japanese Patent Application Kokai 62-29590. These have a structure corresponding to the above formula (A), with a hydroxy or methoxy group at position 5. Position 13 of the ring can be substituted with a 4'-(α-L-oleandrosyl)-α-L-oleandrosyloxy group, as in the avermectins, and there may be a carbon-carbon double bond between positions 22 and 23, or alternatively position 23 may be substituted with a hydroxy group. The substituent at position 25 is of a type not found in the naturally produced milbemycins and avermectins, and includes various α-branched alkyl, alkenyl, alkynyl, alkoxyalkyl, alkylthioalkyl and cycloalkylalkyl groups, or cycloalkyl, cycloalkenyl or heterocyclic groups. This 25-substituent is introduced by adding the corresponding carboxylic acid or derivative thereof to the fermentation broth of an avermectin-producing micro-organism.

The various classes of milbemycin-related macrolide compounds described above are all said to have one or more types of activity as antibiotic, anthelmintic, ectoparasiticidal, acaricidal or other pesticidal agents. However, there is still a continuing need to provide compounds with modified activity against one or more classes of parasites.

OBJECTS OF THIS INVENTION

Accordingly, it is an object of the present invention to provide macrolide compounds having modified parasiticidal activity. It is another object of the invention to provide methods for preparing such compounds. It is a still further object of the invention to provide parasiticidal compositions and methods based on the compounds.

SUMMARY OF THIS INVENTION

It has now been discovered that the activity of milbemycin derivatives can be modified by introducing an unsaturated ester group at the 4-position in place of the 4-methyl group. Specifically, the present invention provides 26-alkenoyloxy derivatives of the milbemycins and related macrolides.

Thus, the invention provides compounds having the formula

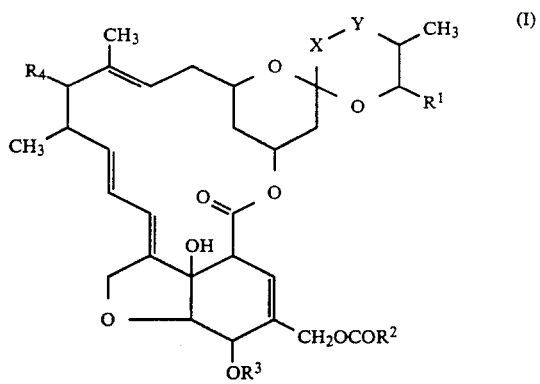

wherein:

—X—Y— represents —$CH_2$—$CH_2$—, —$CH_2$—CHOH—, —CH=CH—, or —$CH_2$—C(=O)—;

$R^1$ represents a methyl group, an ethyl group, an isopropyl group, a sec-butyl group or a group of formula —C($CH_3$)=$CHR^5$ in which $R^5$ represents a methyl group, an ethyl group or an isopropyl group;

$R^2$ represents a group of formula —($CH_2$)$_n$—C($R^6$)=C($R^7$)($R^8$) in which n is 0, 1 or 2, $R^6$ and $R^7$ each represents a hydrogen atom or a methyl group and $R^8$ represents a hydrogen atom, a $C_{1-4}$ alkyl group, a phenyl group or a phenyl group substituted with one or more halogen, methyl or nitro groups;

$R^3$ represents a hydrogen atom, a methyl group, a hydroxy-protecting group or an ester-forming carboxylic or carbonic acid residue; and $R^4$ represents a hydrogen atom or an α-L-oleandrosyl-α-L-oleandrosyloxy group, with the proviso that $R^4$ represents a hydrogen atom when the group $R^1$ represents a methyl group, an ethyl group, or a group of formula —C($CH_3$)=$CHR^5$ in which $R^5$ represents a methyl group, an ethyl group or an isopropyl group.

The invention still further provides a parasiticidal composition which may have an anthelmintic, acaricidal, insecticidal, or other activity. The composition comprises a compound of formula (I) in admixture with a pharmaceutically, agriculturally, veterinarily or horticulturally acceptable carrier or diluent.

The invention still further provides a method of treating or protecting animals (which may be human or non-human) or plants from damage by parasites selected from acarids, helminths and insects, which method comprises applying or administering a compound of formula (I) to said animals, to said plants or to seeds of said plants or to a locus including said animals, plants or seeds.

DETAILED DESCRIPTION OF THE PRESENT INVENTION

In the compounds of formula (I), where $R^2$ represents a group of the formula —C($CH_3$)=$CHR^5$, the group $R^2$ is a 1-methyl-1-propenyl, 1-methyl-1-butenyl or 1,3-dimethyl-1-butenyl group.

Where $R^3$ is a hydroxy-protecting group, it may be any of those conventionally employed for this purpose. For example, the protecting group may be a silyl group represented by the formula Si(R')(R'')(R''') in which R', R'' and R''' each represents a $C_{1-4}$ alkyl group, a benzyl group or a phenyl group. Examples of the silyl group include trimethylsilyl, triethylsilyl, tripropylsilyl, triisopropylsilyl, diisopropylmethylsilyl, t-butyldimethylsilyl, dimethylphenylsilyl, t-butyldiphenylsilyl, triphenylsilyl and tribenzylsilyl groups. Amongst these groups, trimethylsilyl, triethylsilyl and t-butyldimethylsilyl groups are preferred. The protecting group can also be a residue of a carboxylic or carbonic acid residue, as separately mentioned.

When $R^3$ is an acid residue, there is no particular limitation on the nature of the acid, and it can be selected from a wide variety of carboxylic acids and carbonic acids, since it appears that the biological activity of compounds of formula (I) is attributable to the formation of compounds in which —$OR^3$ is a hydroxy group. As mentioned above, the literature contains many examples of suitable acids for forming 5-esterified milbemycins, and such acids can readily be adopted for the compounds of the present invention.

Without being exhaustive, $R^3$ when a residue of an ester-forming carboxylic or carbonic acid can be of the formula —CO—(O)$_n$—$R^{11}$, wherein n is 0 or 1; and $R^{11}$ represents a straight or branched chain $C_{1-18}$ alkyl group, a $C_{3-7}$ cycloalkyl group, a $C_{7-9}$ aralkyl group, a $C_{2-6}$ alkenyl or alkynyl group, a $C_{6-10}$ aryl group or a monocyclic or fused heterocyclic group having from 5 to 10 ring atoms and containing at least one oxygen, sulfur or nitrogen atom. The group $R^{11}$ may optionally have one or more substituents, such as for example an alkyl, alkoxy, alkoxyalkyl, halogen, haloalkyl, alkoxycarbonyl, acyloxy, hydroxy, carboxy, amino, mono- to trialkyl-amino, acylamino, cyano, carbamoyl, mono- or di-alkylcarbamoyl, mercapto, alkylthio, alkylsulfinyl, alkylsulfonyl, nitro, phenoxy, halophenoxy, alkylsulfonyloxy, arylsulfonyloxy, cyanothio group, and 5- or 6-membered heterocyclic groups containing at least one oxygen, sulfur or nitrogen atom. Where the substituent contains a carbon atom or atoms, the number of the carbon atoms is suitably from 1 to 9. Where $R^{11}$ itself is an alkyl, alkenyl or alkynyl group, the substituent is not an alkyl, alkoxyalkyl or haloalkyl group.

Particular examples of acid residues suitable for use as hydroxy-protecting groups include a lower aliphatic acyl group such as a formyl, acetyl, chloroacetyl, dichloroacetyl, trichloroacetyl, trifluoroacetyl, methoxyacetyl, propionyl, n-butyryl, (E)-2-methyl-2-butenoyl, isobutyryl, pentanoyl or pivaloyl group; or an aromatic acyl group such as a benzoyl, o-(dibromoethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl, o-nitrobenzoyl or α-naphthoyl group.

Preferred compounds of formula (I) include those wherein:

(a) —X—Y— is —$CH_2$—$CH_2$—, —$CH_2$—CHOH—, or —$CH_2$—C(=O)—;

(b).(i) $R^1$ is a methyl group, an ethyl group or an isopropyl group and $R^4$ is a hydrogen atom; or (b).(ii) $R^1$ is an isopropyl group or a sec-butyl group and $R^4$ is an α-L-oleandrosyl-α-L-oleandrosyloxy group; or (b).(iii) $R^1$ is a group of formula —C($CH_3$)=$CHR^5$ (in which $R^5$ is as defined above) and $R^4$ is a hydrogen atom;

(c) $R^2$ is a group of formula —CH=C($CH_3$) ($R^{10}$), wherein $R^{10}$ is a methyl group or an ethyl group.

(d) $R^3$ is a hydrogen atom, a lower alkanoyl group having from 1 to 4 carbon atoms (such as an acetyl or propionyl group), or a lower alkoxycarbonyl group having from 2 to 5 carbon atoms (such as an ethoxycarbonyl group).

Particularly preferred compounds are those in which —X—Y— is —$CH_2$—$CH_2$—, $R^1$ is a methyl group or an ethyl group, $R^2$ is a 2-methyl-1-propenyl group, and $R^3$ and $R^4$ are hydrogen atoms.

Specific examples of preferred compounds of this invention include those given in the following table, where the structure is given in terms of the formula (I) which is repeated here for convenience:

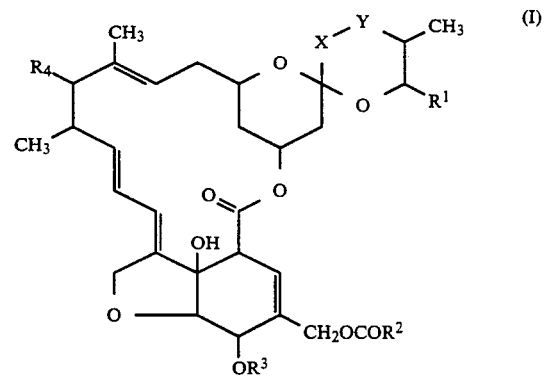

| No. | X-Y | $R_1$ | $R_2$ | $R^3$ | $R^4$ |
|---|---|---|---|---|---|
| 1 | $CH_2$—$CH_2$ | Me | CH=C($CH_3$)$_2$ | H | H |
| 2 | $CH_2$—$CH_2$ | Me | CH=C($CH_3$)($C_2H_5$) | H | H |
| 3 | $CH_2$—$CH_2$ | Et | CH=C($CH_3$)$_2$ | H | H |
| 4 | $CH_2$—$CH_2$ | Et | CH=C($CH_3$)($C_2H_5$) | H | H |
| 5 | $CH_2$—$CH_2$ | Et | CH=$CHCH_3$ | H | H |
| 6 | $CH_2$—$CH_2$ | Et | C($CH_3$)=$CHCH_3$ | H | H |
| 7 | $CH_2$—$CH_2$ | Et | CH=CH($CH_2$)$_2CH_3$ | H | H |
| 8 | $CH_2$—$CH_2$ | Et | CH=CHCH($CH_3$)$_2$ | H | H |
| 9 | $CH_2$—$CH_2$ | Et | $CH_2$CH=$CHC_2H_5$ | H | H |
| 10 | $CH_2$—$CH_2$ | Et | $CH_2CH_2$CH=$CH_2$ | H | H |
| 11 | $CH_2$—$CH_2$ | Et | CH=CH-phenyl | H | H |
| 12 | $CH_2$—$CH_2$ | Et | CH=CH-P-chlorophenyl | H | H |
| 13 | $CH_2$—$CH_2$ | Et | CH=C($CH_3$)$_2$ | BMS | H |
| 14 | $CH_2$—$CH_2$ | Et | CH=C($CH_3$)$_2$ | $COC_2H_5$ | H |
| 15 | $CH_2$—$CH_2$ | Et | CH=C($CH_3$)$_2$ | $COOC_2H_5$ | H |
| 16 | $CH_2$—$CH_2$ | i-Pr | CH=C($CH_3$)$_2$ | H | H |
| 17 | $CH_2$—$CH_2$ | sec-Bu | CH=C($CH_3$)$_2$ | H | α |
| 18 | CH=CH | sec-Bu | CH=C($CH_3$)$_2$ | H | α |
| 19 | $CH_2$—$CH_2$ | DMB | CH=C($CH_3$)$_2$ | H | H |
| 20 | $CH_2$—CHOH | DMB | CH=C($CH_3$)$_2$ | H | H |
| 21 | $CH_2$—C(=O) | DMB | CH=C($CH_3$)$_2$ | H | H |

In this table;

BMS: t-butyldimethylsilyl

α: α-L-oleandrosyl-α-L-oleandrosyloxy

DMB: 1,3-dimethyl-1-butenyl

The compounds of the above table are named as follows:

1. 26-(3-Methyl-2-butenoyloxy)milbemycin $A_3$
2. 26-(3-Methyl-2-pentenoyloxy)milbemycin $A_3$
3. 26-(3-Methyl-2-butenoyloxy)milbemycin $A_4$
4. 26-(3-Methyl-2-pentenoyloxy)milbemycin $A_4$
5. 26-(2-Butenoyloxy)milbemycin $A_4$
6. 26-(2-Methyl-2-butenoyloxy)milbemycin $A_4$
7. 26-(2-Hexenoyloxy)milbemycin $A_4$
8. 26-(4-Methyl-2-pentenoyloxy)milbemycin $A_4$
9. 26-(3-Hexenoyloxy)milbemycin $A_4$
10. 26-(4-Pentenoyloxy)milbemycin $A_4$
11. 26-Cinnamoyloxymilbemycin $A_4$
12. 26-p-Chlorocinnamoyloxymilbemycin $A_4$
13. 5-O-t-Butyldimethylsilyl-2-(3-methyl-2-butenyloxy)milbemycin $A_4$
14. 5-O-Propionyl-2-(3-methyl-2-butenoyloxy)milbemycin $A_4$
15. 5-O-Ethoxycarbonyl-2-(3-methyl-2-butenoyloxy)milbemycin $A_4$
16. 26-(3-Methyl-2-butenoyloxy)milbemycin D
17. 26-(3-Methyl-2-butenoyloxy)ivermectin $B_{1a}$
18. 26-(3-Methyl-2-butenoyloxy)avermectin $B_{1a}$
19. 23-Deoxy-26-(3-methyl-2-butenoyloxy) S-541A
20. 26-(3-Methyl-2-butenoyloxy) S-541A
21. 23-Keto-26-(3-methyl-2-butenoyloxy) S-541A.

Of these compounds, there is a particular preference for Compounds 1, 2, 3, 4, 7, 8, 10, 11, 14, 15, 16, 17, 18, 19, 20 and 21; and especially for Compounds 1, 2, 3, 4, 16, 17, 18, 19, 20 and 21.

The compounds of formula (I) of this invention can be prepared by the steps shown in the following reaction scheme (where the groups —X—Y—, and $R^1$ to $R^4$ are as defined above):

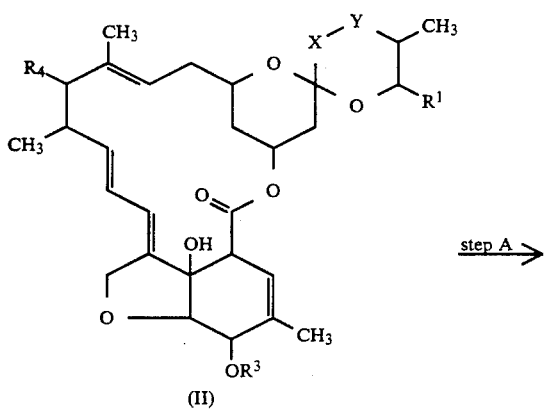

(II)

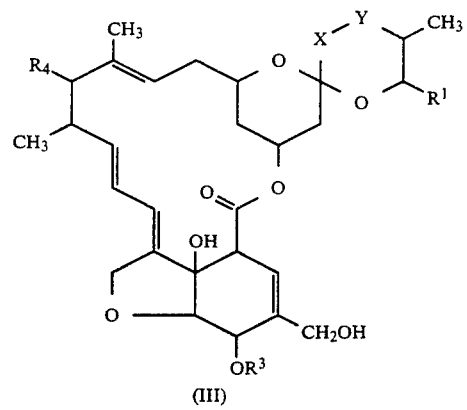

(III)

↓ step B

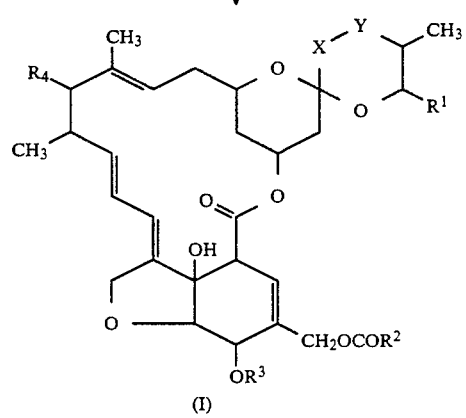

(I)

In the reaction scheme, the step A comprises a selective oxidation of the 4-methyl group, that is to say the methyl group attached to the 4-position of the milbemycin molecule, to yield a 4-hydroxymethyl group. This reaction is known as the "Sharpless reaction" or the "Sharpless oxidation", and is an allyl oxidation using selenium dioxide and t-butylhydroperoxide.

It is already known to apply the Sharpless reaction to macrolides of the type of formula (II), and the reader is now spefically referred to European Patent 74758 and European Patent Specification 237,341, both incorporated herein by reference. Therefore, the present Step A may be performed under conditions similar to those disclosed in these patent specifications.

Thus, the step A involves oxidizing the 4-methyl compound of the formula (II) with t-butyl hydroperoxide in the presence of a catalytic amount of selenium dioxide which oxidizes the 4-methyl group to a 4-hydroxymethyl group and is itself oxidized in the process. The t-butyl hydroperoxide oxidizes the reduced selenium compounds back to selenium dioxide for further oxidation of the molecule. In this way only a small, catalytic amount of the selenium dioxide is required.

The reaction is carried out in an inert solvent which is not susceptible to oxidation. Methylene chloride is preferred, though ethyl acetate, tetrahydrofuran and other solvents may also be employed. The reaction temperature is not critical, and for example it can be from 0° to 50° C. Reaction at room temperature is preferred. The reaction is generally complete in from 1 to 48 hours, and under the preferred conditions the reaction is typically complete in about 24 hours.

The group $R^3$ in the compound of formula (II) is preferably a methyl group, a hydroxy-protecting group or an ester-forming carboxylic or a carbonic acid residue which can act as such a protecting group. Where the group $R^3$ is hydrogen in the compound of formula (II) and is therefore hydrogen in the intermediate product of formula (III), it is preferably converted to one of the other groups before proceeding with the step B, using the procedures described above.

Step B consists in esterification of the 26-hydroxy group of the compound (III) with a carboxylic acid of formula $R^2COOH$ ($R^2$ is as defined above) or a reactive derivative thereof, which may be performed under conditions known per se.

Examples of reactive derivatives include: acid halides such as the acid chloride, acid bromide or acid iodide; acid anhydrides; mixed acid anhydrides; active esters such as the pentachlorophenyl ester or p-nitrophenylester; and active acid amides.

The step B is preferably carried out in the presence of a solvent, the nature of which is not critical, provided that it has no adverse effect upon the reaction.

Examples of suitable solvents include: hydrocarbons, which may be aliphatic or aromatic and which may be halogenated, such as hexane, petroleum ether, benzene, toluene, xylene, chloroform, methylene chloride or chlorobenzene; ethers such as diethyl ether, tetrahydrofuran or dioxane; and esters such as methyl acetate or ethyl acetate. The reaction will take place over a wide range of temperature and the precise temperature chosen is not critical to the invention. The reaction may be conveniently carried out at a temperature of from 0° C. to 100° C. and more preferably at a temperature of from 20° C. to 50° C. The time required for the reaction may vary, depending upon many factors. A period of from 30 minutes to 3 hours will normally suffice.

Generally, from 1 to 10 equivalents, more preferably from 1.5 to 4 equivalents of the acid or its reactive derivative, are used per mole of the compound of formula (III).

Where the acid itself is employed, the reaction is preferably effected in the presence of a dehydrating agent, such as dicyclohexylcarbodiimide (DCC), ethyl polyphosphate (PPE), mesitylenesulfonyl triazolide (MST), p-toluenesulfonic acid or sulfuric acid, more preferably DCC. The amount of dehydrating agent is normally from 1 to 5 equivalents, preferably 1.5 to 4 equivalents. Where DCC is employed, the reaction may conveniently be carried out in the presence of a catalytic amount of a base such as pyridine or 4-pyrrolidinopyridine.

Where a reactive derivative of the acid is employed, the reaction is preferably effected in the presence of a base, more preferably an organic base such as triethylamine, N,N-dimethylaniline, pyridine, 4-dimethylaminopyridine, 1,5-diazabicyclo[4.3.0]nonene-5 (DBN) or 1,8-diazabicyclo[5.4.0]undecene-7 (DBU). The amount of base is normally from 2 to 8 equivalents.

Where the reaction product of Step B bears a silyl protecting group, it can easily be removed to restore the 5-hydroxy group. The deprotection may be achieved by using a dilute acid such as dilute hydrochloric acid or dilute sulfuric acid; an organic acid such as formic acid or acetic acid; p-toluenesulfonic acid/tetrabutylammonium fluoride; or hydrogen fluoride/pyridine; amongst which dilute hydrochloric acid and hydrogen fluoride/pyridine are preferred. The acid is normally in excess, and is preferably from about 2 to 100 equivalents.

The deprotection reaction is preferably carried out in the presence of a solvent, the nature of which is not critical, provided that it has no adverse effect upon the reaction. Examples of suitable solvents include: hydrocarbons, which may be aliphatic or aromatic and which may be halogenated, such as hexane, petroleum ether, benzene, toluene, chloroform, methylene chloride or dichloroethane; ethers such as diethyl ether, tetrahydrofuran, dioxane or dimethoxyethane; alcohols such as methanol or ethanol; nitriles such as acetonitrile or propionitrile; and mixtures of these solvents.

The reaction will take place over a wide range of temperature and the precise temperature chosen is not critical to the invention. However, the reaction may be conveniently carried out at a temperature of from −20° C. to 70° C. and more preferably at a temperature of from −10° C. to 30° C. The time required for the reaction may vary, depending upon many factors; however, a period of from 30 minutes to 24 hours, preferably from 30 minutes to 6 hours, will normally suffice.

A compound of formula (I) where $R^3$ is hydrogen may be subjected to esterification with a carboxylic acid or a carbonic acid, or a reactive derivative thereof, to give a compound esterified at the 5-position.

After completion of the steps of the reaction sequence, the resulting product can be recovered from the reaction mixture by conventional means and, if necessary, may be further purified by such conventional means as the various chromatography techniques, particularly column chromatography. The compound of formula (I) will sometimes be obtained as a mixture of such compounds, and they need not necessarily be separated from each other.

The starting materials of formula (II) are known compounds or may be prepared by methods described in the literature. The reader is referred, for example, to British Patent Specification 1,390,336; Japanese Patent Application Kokai 57-120589; J Am Chem Soc, 1981, 103, 4216; U.S. Pat. Nos. 4,199,569; 4,289,760; British Patent Specification 2,166,436; European Patent Specification 215,654; Belgium Patent 904,709; U.S. Pat. No. Re. 32,034; U.S. Pat. No. 4,457,920; and European Patent 2615; which texts are all incorporated herein by reference.

Conventional procedures can be adopted to convert a compound wherein the group $R^3$ is a hydrogen atom to a desired compound wherein the group $R^3$ takes one of the other meanings. Such conversion is preferably effected before the steps A and B are carried out.

Methylation at the 5-hydroxy position can be achieved using the techniques described, for example, in European Patent Specification 237,341.

Protection of the 5-hydroxy group with a protecting group such as a silyl group can be achieved for instance by reaction with a silyl halide in a solvent, advantageously in the presence of a base.

There is no particular limitation on the nature of the solvent for siliylation, provided that it is inert to the reaction. Preferred solvents include hydrocarbons, such as hexane or benzene; chlorinated hydrocarbons such as methylene chloride, or chloroform; ethers such as diethyl ether; and polar solvents such as tetrahydrofuran, acetonitrile, dimethylformamide, dimethylacetamide, dimethyl sulfoxide or pyridine.

Examples of preferred silylating agents include those of the general formula Si(R')(R'')(R''')Z, in which R', R'' and R''' each represents a $C_{1-4}$ alkyl group, a benzyl group or a phenyl group, and z represents halogen or other suitable cationic counter-ion. Specific examples of preferred silylating agents are trialkylsilyl chloride, triarylsilyl chloride and silyl trifluoromethanesulfonates.

The silylation is typically effected in the presence of a base. The nature of the base is not crucial, but in general organic bases are preferred to inorganic ones. Examples of bases which can be employed include lithium sulfide, imidazole, pyridine, triethylamine and dimethylaminopyridine, particularly imidazole.

Some silylating reagents, such as hexamethyldisilazane, diethyltrimethylsilyl amine, and others work both as the silylating agent and provide their own base, at the same time, and may be adopted for this invention.

Esterification of the 5-hydroxy group with a carboxylic acid or carbonic acid can be carried out using the techniques described for the step B above.

Procedures are also available to enable conversion of compounds wherein —X—Y— has some of the given meanings in to compounds wherein —X—Y— takes some of the other meanings. Such procedures are described, for example, in the European Patent 74,758.

For the starting materials which are natural products, they may take the form of a single isolated compound or a mixture of two or more compounds, which may be used without separation. For example, since mixtures of milbemycins $A_3$ and $A_4$ are readily available and may easily be used, they may be subjected to the reaction sequence without separation.

Some of the compounds of formula (I) of this invention may also be obtained as fermentation products.

Thus, the present invention also provides a process for preparing a compound of formula (I) wherein —X—Y—represents —$CH_2$—$CH_2$—; $R^3$ and $R^4$ each represents a hydrogen atom; and (i) $R^1$ represents a methyl group and $R^2$ represents a 2-methyl-1-propenyl group, (ii) $R^1$ represents a methyl group and $R^2$ represents a 2-methyl-1-butenyl group, or (iii) $R^1$ represents an ethyl group and $R^2$ represents a 2-methyl-1-propenyl group.

Such compounds are referred to herein as milbemycins $\alpha_{11}$ (the possibility (i) given above), $\alpha_{13}$ (the possibility (ii) given above), and $\alpha_{14}$ (the possibility (iii) given above). They may be obtained by cultivation of a productive micro-organism of the genus Streptomyces. Such a micro-organism is the strain SAND 60286 belonging to the genus Streptomyces which was isolated from soil of Miura City, Kanagawa Prefecture, Japan.

The milbemycins $\alpha_{11}$, $\alpha_{13}$, and $\alpha_{14}$ form part of a series of compounds isolated from the fermentation broth of Streptomyces strain SANK 60286 and named milbemycins $\alpha_{11}$ to $\alpha_{15}$, as shown in the table below.

|  | $R^1$ | $R^2$ |
| --- | --- | --- |
| $\alpha_{11}$ | methyl | 2-methyl-1-propenyl |
| $\alpha_{12}$ | methyl | isobutyl |
| $\alpha_{13}$ | methyl | 2-methyl-1-butenyl |
| $\alpha_{14}$ | ethyl | 2-methyl-1-propenyl |
| $\alpha_{15}$ | ethyl | isobutyl |

Characteristics of Streptomyces SANK 60286

The mycological properties of actinomycetes strain SANK 60286 are as follows.

1. Morphological characteristics

This strain is found microscopically to have branched, pale yellow to yellowish brown basal mycelia from which white to yellowish gray aerial mycelia elongate with spiral terminals. In a grown spore chain, 10 or more spores are observed in a line, and the spores have warty-rugose surfaces. The strain forms, in some kinds of media, clear gold slime on the surface of aerial mycelium, and this slime changes to yellowish spots with the culturing process. Sometimes blackish spots are formed due to humidity at the later stage of culture.

2. Growth on various media

This strain exhibited the properties shown below after culturing at 28° C. for 14 days on various media. The color names and numbers used herein were assigned on the basis of the "Guide to Color Standard", a manual published by Nippon Shikisai Kenkyusho.

| medium | property* | characteristics |
| --- | --- | --- |
| sucrose-nitrate agar | G | good, grayish white (N-9) |
|  | AM | good, white |
|  | R | yellowish gray |
|  | SP | none |
| glucose-asparagine agar | G | very good, yellowish gray (2-9-11) |
|  | AM | good, grayish white (N-9) |
|  | R | pale yellow (3-9-10) |
|  | SP | none |
| glycerol-asparagine agar (ISP 5) | G | good, yellowish brown (2-9-11) |
|  | AM | good, white to yellowish gray (2-9-11) |
|  | R | pale yellow (8-9-11) |
|  | SP | none |
| inorganic-starch salt agar (ISP 4) | G | very good, light olive (6-8-11) |
|  | AM | abundant, white to light olive gray (4-8-11) |
|  | R | yellowish brown (2-9-11) |
|  | SP | none |
| tyrosine agar (ISP 7) | G | good, light olive gray (2-8-11) |
|  | AM | good, white to pale yellow (3-9-10) |
|  | R | pale yellow (6-8-10) |
|  | SP | none |
| peptone-yeast extract-iron agar (ISP 6) | G | good, yellowish gray (2-9-12) |
|  | AM | good, white |
|  | R | yellowish gray (4-9-11) |
|  | SP | none |
| nutrient agar (Difco) | G | good, yellowish gray (1-9-10) |
|  | AM | slight formation, gray (N-9) |
|  | R | pale yellow (3-9-10) |
|  | SP | none |
| yeast-extract-malt-extract agar (ISP 2) | G | very good, yellowish brown (2-9-11) |
|  | AM | abundant, grayish white (N-9) |
|  | R | reddish yellow (12-8-9) |
|  | SP | pale yellow (8-9-12) |
| oatmeal agar (ISP 3) | G | very good, pale yellow (8-9-12) |
|  | AM | Abundant, grayish white (N-8) |
|  | R | yellowish brown (2-9-11) |
|  | SP | light olive gray (4-7-11) |
| water agar | G | poor, grayish white (N-9) |
|  | AM | slight formation, light brownish gray (2-8-8) |
|  | R | grayish white (N-9) |
|  | SP | none |
| potato extract-carrot extract agar | G | poor, grayish white (N-9) |
|  | AM | good, light brownish gray (2-8-8) |
|  | R | pale yellowish orange |

-continued

| medium | property* | characteristics |
|---|---|---|
| | SP | (2-9-9)<br>none |

*G: growth
AM: aerial mycelium
R: reverse surface
SP: soluble pigment

3. Physiological properties

The physiological properties of strain SANK 60286 are shown below.

| | |
|---|---|
| hydrolysis of starch | positive |
| liquefaction of gelatin | positive (weak) |
| reduction of nitrate | positive |
| coagulation of milk<br>(at 28° C. and 37° C.) | positive (weak) |
| peptonization of milk<br>(at 28° C. and 37° C.) | positive (weak) |
| range of growing temperature<br>(medium 1)* | 18–37° C. |
| production of melanoid pigment | |
| (medium 2) | negative |
| (medium 3) | negative |
| (medium 4) | negative |

*medium 1: yeast extract-malt extract agar (ISP 2)
medium 2: tryptone-yeast extract-broth (ISP 1)
medium 3: peptone-yeast extract-iron agar (ISP 6)
medium 4: tyrosine agar (ISP 7)

After culturing at 28° C. for 14 days on Pridham-Gottlieb agar medium, SANK strain 60286 showed utilization of carbon sources as shown in the table below.

| sugar | utilization |
|---|---|
| D-glucose | ++ |
| L-arabinose | ++ |
| D-xylose | + |
| i-inositol | ++ |
| D-mannitol | ++ |
| D-fructose | ++ |
| L-rhamnose | ++ |
| sucrose | ++ |
| raffinose | ++ |
| control | — |

++ well utilized
+ utilized
— not utilized

4. Cell components

The cell wall of strain SANK 60286 was examined according to the method reported by B Becker et al. (Applied Microbiology 12, 421 (1964)). Since L,L-diaminopimelic acid and glycine could be detected, the cell wall was shown to be cell wall type I. Sugar components in the whole cells were then examined according to the method reported by M P Lechevalier (Journal of Laboratory & Clinical Medicine 71, 934 (1968)). No characteristic pattern was observed.

In summary, the strain was shown to belong to the genus Streptomyces of the actinomycetes.

Identification of Streptomyces strain SANK 60286 was performed according to the standard of ISP (The International Streptomyces Project); Bergey's Manual of Determinative Bacteriology, Eighth Edition; The Actinomycetes by S A Waksman; and other recent references on actinomycetes.

When the properties of strain SANK 60286 were compared with those of other known species of the genus Streptomyces, the morphological and physiological ones were nearly identical with those of *Streptomyces hygroscopicus* subsp *aureolacrimosus* (J Antibiotics 36, 438 (1983)).

A small difference was observed, however, in culture properties between the two strains. It is well-known that the properties of actinomycetes change in some degree even for the same strain after successive cultures. Therefore, strains cannot always be differentiated taxonomically because of a slight difference in culture properties.

For these reasons, strain SANK 60286 which produces milbemycins $\alpha_{11}$, $\alpha_{12}$, $\alpha_{13}$, $\alpha_{14}$ and $\alpha_{15}$ has been identified as *Streptomyces hygroscopicus* subsp *aureolacrimosus* SANK 60286. This strain has been deposited in accordance with the provision of the Budapest Treaty on Oct. 20, 1986 at the Fermentation Research Institute, Japan, and given the accession number FERM BP-1190. Samples of the strain will be available under the relevant provisions of the Budapest Treaty.

Actinomycetes including *Streptomyces hygroscopicus* subsp *aureolacrimosus* SANK 60286 readily undergo mutation both through natural causes and as a result of artificial treatments such as UV irradiation, radiation treatment and chemical treatment. The present invention embraces all productive mutants of strain SANK 60286. These mutant strains also include any strains obtained by gene manipulation such as gene recombination, transduction and transformation. In other words, this invention includes all such strains that can produce one or more of milbemycins $\alpha_{11}$, $\alpha_{13}$, and $\alpha_{14}$, and especially strains that can not be clearly differentiated from strain SANK 60286 or its mutants.

Milbemycins $\alpha_{11}$, $\alpha_{13}$, and $\alpha_{14}$ can be obtained by culturing strain SANK 60286 in a suitable medium and by collecting milbemycins from the medium. Conventional substances generally employed for the culture of micro-organisms of the genus Streptomyces can be used as the nutrients. For example, the carbon source can be glucose, sucrose, starch, glycerin, thick malt syrup, molasses or soybean oil. Further by way of example, the nitrogen source can be soybean powder, wheat germ, meat extract, peptone, yeast cells, corn steep liquor, ammonium sulfate or sodium nitrate. If necessary, organic and inorganic additives which promote the growth of micro-organisms and activate the production of milbemycins $\alpha_{11}$, $\alpha_{13}$, and $\alpha_{14}$ may be used in a suitable combination, as well as inorganic salts such as calcium carbonate, sodium chloride, potassium chloride and phosphates.

In a similar manner to the conventional methods employed for production of antibiotics, liquid culture, in particular deep liquid culture, is most suitable for the culturing of the micro-organism. The culture is conducted aerobically. A suitable temperature for the culture is from 22° to 30° C., and in most cases the culture is carried out at around 28° C. Production of milbemycins $\alpha_{11}$, $\alpha_{13}$, and $\alpha_{14}$ typically reaches a maximum after 5 to 15 days, either by shake culture or tank culture.

The production of milbemycins $\alpha_{11}$, $\alpha_{13}$, and $\alpha_{14}$ can be monitored by the following procedure. One ml of the cultured material is taken in a small tube, 9 ml of 80% aqueous methanol is added. The tube is shaken and centrifuged. High performance liquid chromatography (such as a H-2151, ODS reverse phase column, Senshu Co. 6×150 mm, and a pump Model 655, Hitachi) is employed. Five $\mu$l of the sample is injected, and developed with a mixed solvent of acetonitrile and water (80:20) at a flow rate of 1.5 ml/min. Milbemycins $\alpha_{11}$, $a_{13}$, and $a_{14}$ are monitored by an UV detector (240 nm) and determined by a data processing unit (such as a Union Tech Inst MCPD-350PC).

For collecting milbemycins $a_{11}$, $a_{13}$, and $a_{14}$ from the culture medium, an adsorbent such as active carbon, alumina or silica gel; a synthetic adsorbent such as Diaion HP-20 (Mitsubishi Chem. Ind. Ltd.); an adsorbent such as Avicel (Asahi Chem. Ind. Co., Ltd.) or filter paper; an ion exchange resin; or an ion exchange gel filtering material can be employed. Most effective is the following procedure:

The cultured material is filtered using a filter aid such as diatomite. The cake obtained is extracted with methanol to dissolve the desired compounds in aqueous methanol. Water is added, and the mix extracted with hexane. The hexane solution is evaporated under reduced pressure to give an oily substance which contains milbemycins $a_{11}$, $a_{13}$, and $a_{14}$. The oily substance containing milbemycins $a_{11}$, $a_{13}$, and $a_{14}$ is adsorbed on a Lobar column Si60 (Merck, size B) and eluted with a mixed solvent of hexane and ethyl acetate (8:2) to collect fractions each containing milbemycins $a_{11}$, $a_{13}$, or $a_{14}$. Each fraction containing any one of the milbemycins is evaporated under reduced pressure to give an oily substance. The oil is mixed with a small amount of methanol, adsorbed onto a Lobar column RP-8 (Merck, size B), and eluted with a mixed solvent of acetonitrile and water (80:20). The fractions each containing one of these compounds are collected and, after distilling off acetonitrile under a reduced pressure, extracted with ethyl acetate. Finally, by HPLC (reverse phase column), each of milbemycins $a_{11}$, $a_{13}$, and $a_{14}$ can be obtained as a powder. The milbemycins $a_{12}$ and $a_{15}$ can also be obtained in a similar manner.

The compounds of formula (I) of this invention have excellent acaricidal activity against adults and eggs of the two spotted spider mite (Tetranychus), citrus red mite (Panonychus), European red mite (Panonychus) and rust mites which are parasitic to fruit trees, vegetables and flowering plants, and against Ixodidae, Dermanysside, Sarcoptidae and other parasites which are parasitic to animals. The compounds have, in addition, activity against Oestrus, Lucilia, Hypoderma, Gautrophilus; fleas, and lice, among others which are parasitic to animals and birds; domestic insects such as cockroaches, houseflies and other insects; and various harmful insects in agriculture and horticulture area such as aphids, diamondback moth and larvae of Lepidoptera. The compounds of this invention further have activity against Meloidogyne, Bursaphelenchus, Rhizoglyphus and other species in soil.

In addition, the compounds of this invention have excellent parasiticidal activity against endoparasites on animals and humans. In particular, the compounds are effective not only against nematodes parasitic to domestic animals, poultry and pets such as pigs, sheep, goats, cattle, horses, dogs, cats and fowls, but also against parasites belonging to Filariidae or Setariidae and parasites found in the digestive tract, blood and other tissues and organs of humans.

When the compounds of this invention are intended to be employed for agricultural and horticultural purposes, they can be formulated as preparations conventionally used for agricultural chemicals such as dusts, wettable powders, emulsifiable concentrates, aqueous or oily suspensions and aerosols, by mixing them with carriers or any other auxiliary agents if necessary. The carriers may be natural or synthetic, and inorganic or organic substances which are incorporated in agricultural formulations in order to assist the active ingredient to reach its target site, and to make it easier to store, transport and handle the active ingredient.

As for suitable solid carriers, there may be mentioned inorganic substances such as clays (for example, kaolinite, montmorillonite and attapulgite), talc, mica, pyrophylite, pumice, vermiculite, gypsum, calcium carbonate, dolomite, diatomaceous earth, magnesium carbonate, apatite, zeolite, silicic anhydride and synthetic calcium silicate; vegetable organic substances such as soybean powder, tobacco powder, walnut powder, wheat flour, wood meal, starch and crystalline cellulose; synthetic or natural high molecular compounds such as cumarone resins, petroleum resins, alkyd resins, polyvinyl chloride, polyalkylene glycols, ketone resins, ester gums, copal gums and dammar gums; waxes such as carnauba wax and beeswax; and urea.

As for suitable liquid carriers, there may be mentioned paraffinic or naphthenic hydrocarbons such as kerosene, mineral oil, spindle oil and white oil; aromatic hydrocarbons such as benzene, toluene, xylene, ethylbenzene, cumene and methylnaphthalene; chlorinated hydrocarbons such as carbon tetrachloride, chloroform, trichloroethylene, monochlorobenzene and o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol, diethylene glycol, cyclohexanol and benzyl alcohol; ether alcohols such as ethylene glycol ethyl ether, ethylene glycol phenyl ether, diethylene glycol ethyl ether and diethylene glycol butyl ether; polar solvents such as dimethylformamide and dimethylsulfoxide; and water.

As for suitable gaseous carriers, air, nitrogen, carbon dioxide and Freon (trade mark) gas may be mentioned. These gases may be mixed for spraying.

In order to improve such properties of the formulations as dispersion, emulsification, spreading, penetration and adherence, various kinds of surface active agents and high molecular compounds may be added if necessary, by which wettability, adhesion and absorption of the formulation to animal and plant can be strengthened for increase in the effectiveness.

As for surface active agents employable for emulsification, dispersion, wettability, spreading, binding, disintegration control, stabilization of the active ingredients, fluidity improvement and rust prevention, any of non-ionic, anionic, cationic and amphoteric types may be used, but among these non-ionic and/or anionic surface active agents are usually used. As for suitable non-ionic surface active agents, there may be mentioned, for example, the polymerization adducts of ethylene oxide with higher alcohols such as lauryl alcohol, stearyl alcohol, and olealyl alcohol; the polymerization adducts of ethylene oxide with alkylphenols such as iso-octylphenol and nonylphenol; the polymerization adducts of ethylene oxide with alkylnaphthols such as butylnaphthol and octylnaphthol; the polymerization adducts of ethylene oxide with higher fatty acids such as palmitic acid, stearic acid and oleic acid; the polymerization adducts of ethylene oxide with mono- or dialkylphosphoric acid such as stearylphosphoric acid and dilaurylphosphoric acid; the polymerization adducts of ethylene oxide with amines such as dodecylamine and stearic amide; higher fatty acid esters of polyalcohols such as sorbitan and the polymerization adducts of ethylene oxide therewith; and the polymerization adducts of ethylene oxide with propylene oxide. As for suitable anionic surface active agents, there may be mentioned, for example, alkyl sulfate (ester) salts such as sodium lauryl sulfate and amine salts of oleyl alcohol sulfuric acid ester; alkyl sulfonates such as sodium salt of sulfosuccinic acid dioctyl ester and sodium 2-ethylhexenesulfonate; and aryl sulfonates such as sodium isopropylnaphthalenesulfonate, sodium methylene bis-naphthalenesulfonate, sodium lignin-sulfonate and sodium dodecylbenzenesulfonate.

In order to improve the properties of the formulation and to enhance the biological effect, the compositions of this invention may be used in combination with high molecular compounds or other auxiliary substances such as casein, gelatin, albumin, glue, sodium alginate, carboxymethyl cellulose, methyl cellulose, hydroxyethyl cellulose and polyvinyl alcohol.

The above-mentioned carriers and various auxiliary substances may be used alone or in any desired combination depending on the type of formulation, application target and the like factors.

Dusts may contain, for example, from 1 to 25% by weight of active ingredient in general, and a solid carrier as the remainder.

Wettable powders may contain, for example, from 10 to 90% by weight of active ingredient in general, and a solid carrier and dispersing and wetting agent as the remainder. If necessary, a protective colloid agent, thixotropic agent and antiforming agent may be added.

Emulsifiable concentrates may contain, for example, from 5 to 50% by weight of active ingredient in general and from 5 to 20% by weight of emulsifying agent, and a liquid carrier as the remainder. If necessary, an anticorrosive agent may be added.

Oil formulations may contain, for example, from 0.5 to 5% by weight of active ingredient in general and a liquid carrier such as kerosene as the remainder.

Aerosols may contain, for example, from 0.1 to 5% by weight of active ingredient in general, and optionally a perfume, and an oily and/or liquid carrier as the remainder. Propellants such as liquified petroleum gas, a fluorocarbon gas and carbon dioxide may be charged.

After being formulated variously as mentioned above, the composition of this invention may be effectively applied to the crops and domestic animals parasitized with harmful insects or mites in paddy field, orchard and upland field, by treating the stems and leaves of crops, soil or domestic animals at a concentration from 0.5 to 100 ppm of the active ingredient.

When the compounds of this invention are intended to be employed for animals and humans as an anthelmintic agent, the compounds may be orally given in the form of drink. The drink is usually a solution, suspension or dispersion with a suitable non-toxic solvent or water together with a suspending agent such as bentonite and a wetting agent or any other vehicles. In general, the drink contains also an antifoaming agent. The drink composition contains generally from about 0.01 to 0.5%, preferably from 0.01 to 0.1%, by weight of the active ingredient.

When the compounds of this invention are intended to be given to animals in the form of feed, the compounds may be used by dispersing these homogeneously into feed, by top-dressing or in the form of pellets. In order to obtain the desired anthelmintic effect, the active ingredients should be present in general from 0.0001 to 0.02% as the final content in feed.

The compounds of this invention can be also administered parenterally to animals by injection into the forestomach, muscle, trachea or by subcutaneous injection, dissolved or dispersed in a liquid carrier vehicle. For the parenteral administration, the active compounds may be preferably mixed with a suitable vegetable oil such as peanut oil or cotton oil. Such a kind of formulation generally contains from 0.05 to 50% by weight of the active ingredient.

The compounds of this invention can also be administered locally by mixing them with a suitable carrier such as dimethylsulfoxide or a hydrocarbon solvent. This kind of formulation can be applied directly to the surface of the animal body by using a spray or by direct injection.

The most suitable oral dosage for obtaining the best result depends on the kind of animal to be treated and the type and degree of parasitic infection. Generally, the dosage is from 0.01 to 100 mg, preferably from 0.5 to 50.0 mg, per 1 kg of animal body weight. The dosage may be given singly or by several divided doses for a relatively short period like from 1 to 5 days.

EXAMPLES OF THE INVENTION

The present invention is illustrated in more detail by the following non-limiting examples.

EXAMPLE 1 milbemycins $\alpha_{11}$, $\alpha_{13}$ and $\alpha_{14}$
(Compounds No 1, 2 and 3)

In each of ten 500-ml Erlenmeyer flasks, 100 ml of a preculture medium containing sucrose, polypeptone and $K_2HPO_4$ (1%, 0.35% or 0.05%), respectively, were inoculated with one loopful of *Streptomyces hygroscopicus* subsp *aureolacrimosus* SANK 60286. After culture on a rotary shaker for 48 hours at 28° C., 1 liter of the culture liquid was transplanted into two 30-liter jar fermenters each containing 20 liters of production medium (sucrose 8%, soybean powder 1%, skimmed milk 1%, yeast extract 0.1%, meat extract 0.1%, $CaCO_3$ 0.3%, $K_2HPO_4$ 0.03%, $MgSO_4.7H_2O$ 0.1%, $FeSO_4.7H_2O$ 0.005%, pH before sterilization 7.2).

The culture was carried out at 28° C. for 12 days in the jar fermenters at a sterilized air flow of 0.5 vvm, under an internal pressure of 0.5 kg cm$^{-2}$, at a rotation of 40 to 180 rpm and a DO value of 4 to 7 ppm. Thirty two liters of the cultured material was mixed with 1.8 kg of celite, and filtered. The mycelial cake was washed with 5 liters of water and the filtrate and washings were discarded. The mycelial cake was mixed with 20 l of methanol for 1 hour and after filtration again washed with 5 liters of methanol.

The filtrate and washings were collected and evaporated under a reduced pressure to give about 2 liters of aqueous residual liquid. This liquid was extracted three times with 2 liters of hexane. The hexane layer was washed three times with 1 liter of 2% sodium hydroxide solution. The hexane layer was dried over anhydrous sodium sulfate and filtered. The filtrate was evaporated to give 38 g of an oily substance. Twenty g of this oily substance was dissolved in 500 ml of hexane. The solution was loaded on to a column which had been prepared from 300 g of silica gel (Mallinckrodt Inc. Silica Type 60) with hexane treatment, and developed with 2 liters of hexane then with hexane/ethyl acetate (3:1).

By monitoring eluted fractions using HPLC, milbemycins $\alpha_{11}$, $\alpha_{12}$, $\alpha_{13}$, $\alpha_{14}$ and $\alpha_{15}$ were collected as a mixture. Evaporation of the solvent gave 1.9 g of oily crude product. The whole product was dissolved in 10 ml of 50% methanol/water. The solution was loaded on a column which was prepared from 160 g of silanated silica gel (Merck Co., Art 7719) treated with 50% methanol/water, and developed with 60% methanol/water, then with 70% methanol/water, and finally with 80% methanol/water. By monitoring the eluted fractions with HPLC, the milbemycins $\alpha_{11}$, $\alpha_{12}$, $\alpha_{13}$, $\alpha_{14}$ and $\alpha_{15}$ were obtained as a mixture.

Evaporation of the solvent gave 840 mg of an oily crude product. The whole product was dissolved in 20 ml of acetonitrile. The acetonitrile solution was subjected to preparative HPLC using a reverse phase column (Senshu Co., ODS, H-5251, 20×250 mm). 1 ml samples of the solution were charged each time, and developed with 80% acetonitrile/water at a flow rate of 9.9 ml/min. By monitoring the fractions using UV at 240 nm, the fractions containing product were obtained. From each such fraction, the solvent was distilled off. Lyophilization of the aqueous residual liquid gave 128 mg of $\alpha_{11}$, 11.7 mg of $\alpha_{12}$, 14.8 mg of $\alpha_{13}$, 43 mg of $\alpha_{14}$ and 3 mg of $\alpha_{15}$ in the order eluted, and each as a powdery substance.

milbemycin $\alpha_{11}$
elementary analysis (%): C=68.83, H=8.32
molecular weight: 626 (measured by electron bombardment mass spectrum. The same applies hereafter.)
molecular formula: $C_{36}H_{50}O_9$
specific rotation: $[\alpha]^{23}= +104.3°$ (C=1.05, CHCl$_3$) (measured using the sodium-D line. The same applies hereafter.)
UV absorption spectrum: $\lambda_{max}$ (CH$_3$OH) nm (E$^{1\%}$, cm$^{-1}$): 230 (sh), 238 (990), 244 (990), 252 (sh)
IR absorption spectrum: $\nu_{max}$ (KBr) cm$^{-1}$: 3450, 2950, 1715, 1650, 1450, 1380, 1330, 1270, 1220, 1180, 1160, 1140, 1090, 1080, 1050, 1020, 990, 940, 850
proton nuclear magnetic resonance spectrum (CDCl$_3$, 270 MHz): 1.90 (3H, singlet, trans-CH$_3$—C(CH$_3$)=CH—COO—) 2.15 (3H, singlet, cis-C$\underline{H}_3$—C(CH$_3$)=CH—COO—) 3.27 (1H, doublet of quartets, C$_{25}$H) 4.00 (1H, doublet, J=6 Hz, C$_6$H) 4.65–4.90 (4H, multiplet, C$_{26}$H, C$_{27}$H)
electron bombardment mass spectrum: m/Z=626 (M+), 558, 526, 508, 400, 181, 153 HPLC retention time: 13.4 minutes (ODS, H-2151, 6×150 mm, Senshu Co., developing solvent 80% acetonitrile/water, flow rate 1.5 ml/min, monitoring at UV 240 nm. The same conditions apply hereafter.)

milbemycin $\alpha_{12}$
elementary analysis (%): C=67.04, H=8.01
molecular weight: 628
molecular formula: $C_{36}H_{52}O_9$
specific rotation: $[\alpha]^{23}= +118.3°$ (C=1.0, CHCl$_3$)
UV absorption spectrum: $\lambda_{max}$ (CH$_3$OH) nm (E$^{1\%}$, cm$^{-1}$): 238 (750), 244(810), 253 (sh)
IR absorption spectrum: $\nu_{max}$ (KBr) cm$^{-1}$: 3500, 2950, 1740, 1710, 1450, 1380, 1330, 1290, 1180, 1120, 1090, 1050, 990
electron bombardment mass spectrum: m/Z=628, 556, 548, 525, 400, 382, 329, 181, 153 HPLC retention time: 14.6 minutes milbemycin $\alpha_{13}$
elementary analysis (%): C=67.41, H=8.12
molecular weight: 640
molecular formula: $C_{37}H_{52}O_9$
specific rotation: $[\alpha]^{23}= +91.6°$ (C=0.89, CHCl$_3$)
UV absorption spectrum: $\lambda_{max}$ (CH$_3$OH) nm (E$^{1\%}$, cm$^{-1}$): 230 (sh), 237 (805), 245 (795), 253 (sh)
IR absorption spectrum: $\nu_{max}$ (KBr) cm$^{-1}$: 3500, 2950, 1720, 1650, 1450, 1380, 1340, 1310, 1270, 1210, 1180, 1140, 1115, 1095, 1050, 990, 960, 940, 860
proton nuclear magnetic resonance spectrum (CDCl$_3$, 270 MHz): 1.07 (3H, triplet, CH$_3$CH$_2$—C(CH$_3$)=CH—COO—) 2.16 (3H, singlet, C$\underline{H}_3$—C(C$_2$H$_5$)=CH—COO—) 3.27 (1H, doublet of quartets, C$_{25}$H) 4.00 (1H, doublet, J=6 Hz, C$_6$H) 4.65–4.90 (4H, multiplet, C$_{26}$H, C$_{27}$H)
electron bombardment mass spectrum: M/Z=640 (M+), 526, 508, 276, 181, 153
HPLC retention time: 16.4 minutes milbemycin $\alpha_{14}$
elementary analysis (%): C=67.62, H=7.84
molecular weight: 640
molecular formula: $C_{37}H_{52}O_9$
specific rotation: $[\alpha]^{23}= +96.1°$ (C=1.14, CHCl$_3$)
UV absorption spectrum: $\lambda_{max}$ (CH$_3$OH) nm (E$^{1\%}$, cm$^{-1}$): 230 (sh), 237 (800), 244 (810), 253 (sh)
proton nuclear magnetic resonance spectrum (CDCl$_3$, 270 MHz): 3.09 (1H, doublet of triplets, J=2.4, 9.3 Hz, C$_{25}$H) 4.00 (1H, doublet, J=6.6 Hz, C$_6$H) 4.64–4.88 (4H, multiplet, C$_{26}$H, C$_{27}$H) 5.81 (1H, broad singlet, C$_3$H)
IR absorption spectrum: $\nu_{max}$ (KBr) cm$^{-1}$: 3450, 2950, 1720, 1650, 1450, 1380, 1340, 1270, 1220, 1180, 1140, 1100, 1060, 1030, 990, 960, 860
electron bombardment mass spectrum: m/Z=640, 540, 522, 276, 263, 195, 167
HPLC retention time: 18.0 minutes milbemycin $\alpha_{15}$
molecular weight: 642
molecular formula: $C_{37}H_{54}O_9$
electron bombardment mass spectrum: m/Z=642, 555, 540, 414, 396, 385, 356, 314, 264, 245, 195, 167
HPLC retention time: 19.6 minutes

EXAMPLE 2

5-O-t-Butyldimethylsilylmilbemycin $\alpha_{14}$
(Compound No 13)

150 μl of pyridine and 200 μl of 3-methyl-2-butenoyl chloride were added to a solution of 319.3 mg of 26-hydroxy-5-O-t-butyldimethylsilylmilbemycin A$_4$ in 10 ml of methylene chloride cooled at 0° C. The mixture was then stirred for 30 minutes. The reaction mixture was poured into a saturated aqueous solution of sodium hydrogencarbonate and extracted with methylene chloride. The extract was dried over anhydrous magnesium sulfate and concentrated by evaporation.

The residue was purified by column chromatography through silica gel to give 326.2 mg of the title compound (91% yield).

Mass spectrum (EI Method, m/z): 754 (M+), 736, 715, 697, 654, 636, 597, 589

Nuclear magnetic resonance spectrum (270 MHz, CDCl$_3$, δ ppm): 0.11 (3H, singlet, SiCH$_3$) 0.13 (3H, singlet, SiCH$_3$) 3.07 (1H, doublet of triplets, J=2.4, 9.3 Hz, C$_{25}$H) 3.85 (1H, doublet, J=5.6 Hz, C$_6$H) 5.78 (1H, singlet, C$_3$H)

EXAMPLE 3

Milbemycin $\alpha_{14}$
(Compound No 3)

2.5 ml of 68% hydrogen fluoride in pyridine were added to a solution of 302.8 mg of 5-O-t-butyldimethylsilylmilbemycin $\alpha_{14}$ in 15 ml of acetonitrile cooled at 0° C., then the mixture was stirred for 2.5 hours. At the end of this time, about 300 mg of potassium carbonate and water were added to the reaction mixture in this order, and then the mixture was extracted with chloroform. The extract was dried over anhydrous magnesium sulfate and concentrated by evaporation. The residue was purified by column chromatography through silica gel to give 232.2 mg of the title compound (90% yield) matching the properties of the milbemycin $\alpha_{14}$ prepared in Example 1.

EXAMPLE 4

26-(2-Butenoyloxy)milbemycin $A_4$
(Compound No 5)

24 μl of pyridine and 39 μl of 2-butenoyl chloride were added to a solution of 150 mg of 26-hydroxy-5-O-t-butyldimethylsilylmilbemycin $A_4$ in 2 ml of methylene chloride cooled at 0° C., then the mixture was stirred at room temperature for 3 hours. The reaction mixture was poured into ice-water and extracted with ethyl acetate. The extract was dried over anhydrous sodium sulfate and concentrated by evaporation. The residue was dissolved in 4 ml of acetonitrile which was then cooled to 0° C. 0.5 ml of 68% hydrogen fluoride in pyridine was added to the solution and the mixture was stirred at room temperature for 1.5 hours. At the end of this time, the reaction mixture was poured into ice-water and extracted with ethyl acetate. The extract was washed with a saturated aqueous solution of sodium hydrogencarbonate, dried over anhydrous sodium sulfate and concentrated by evaporation. The residue was purified by preparative thin layer chromatography to give 66.5 mg of the title compound (48% yield).

Mass spectrum (EI Method, m/z): 626 (M+), 540, 522, 414, 264, 245, 191, 167, 151

Nuclear magnetic resonance spectrum (270 MHz, $CDCl_3$, δ ppm): 1.99 (3H, doublet of doublets, J=6.9, 1.6 Hz, C$\underline{H}$—CH$_3$=CH—COO—) 3.08 (1H, doublet of triplets, J=2.4, 9.3 Hz, $C_{25}H$) 4.84 (1H, doublet, J=13.3 Hz, $C_{26}H$) 5.87 (1H, quartet of doublets, J=1.6, 15.3 Hz, CH—CH$_3$=C$\underline{H}$—COO—) 7.03 (1H, quartet of doublets, J=6.9, 15.3 Hz, CH—C$\underline{H}_3$=CH—COO—)

EXAMPLE 5

26-(3-Methyl-2-butenoyloxy)milbemycin D
(Compound No 16)

0.15 ml of 3-methyl-2-butenoyl chloride was added to a solution of 177.3/mg of 26-hydroxy-5-O-t-butyldimethylsilylmilbemycin D and 0.1 ml of pyridine in 15 ml of methylene chloride cooled at 0° C. The mixture was then stirred for 2 hours. The reaction mixture was poured into a saturated aqueous solution of sodium hydrogencarbonate and extracted with methylene chloride. The extract was dried over anhydrous magnesium sulfate and concentrated by evaporation. The residue was dissolved in 10 ml of acetonitrile which was then cooled to 0° C. 1 ml of 68% hydrogen fluoride in pyridine was added to the solution and the mixture was stirred for 2 hours. At the end of this time, the reaction mixture was poured into a saturated aqueous solution of sodium hydrogencarbonate and extracted with ethyl acetate. The extract was dried over anhydrous magnesium sulfate and concentrated by evaporation. The residue was purified by column chromatography through silica gel to give 144.7 mg of the title compound (86% yield).

Mass spectrum (EI Method, m/z): 654 (M+), 618, 554, 428, 410, 356

Nuclear magnetic resonance spectrum (270 MHz, $CDCl_3$, δ ppm): 3.07 (1H, broad doublet, J=7.7 Hz, $C_{25}H$) 4.48 (1H, broad doublet, J=4.0 Hz, $C_5H$) 4.68 (1H, doublet, J=14.7 Hz, $C_{26}H$) 4.79 (1H, doublet, J=14.7 Hz, $C_{26}H$)

The following compounds were prepared, substantially by following any one of the appropriate methods described in Examples 2 to 5.

EXAMPLE 6

26-(2-Methyl-2-butenoyloxy)milbemycin $A_4$
Compound No 6

Mass spectrum (EI Method, m/z): 640 (M+), 604, 540, 522, 414

Nuclear magnetic resonance spectrum (270 MHz, $CDCl_3$, δ ppm): 1.80 (3H, doublet, J=7.2 Hz, CH$_3$—CH=C(CH$_3$)—COO—) 1.85 (3H, singlet, C$\underline{H}_3$—CH=C(CH$_3$)—COO—) 3.08 (1H, doublet of triplets, J=2.4, 9.3 Hz, $C_{25}H$) 4.73 (1H, doublet, J=13.7H, $C_{26}H$)

EXAMPLE 7

26-(2-Hexenoyloxy)milbemycin $A_4$
Compound No 7

Mass spectrum (EI Method, m/z): 654 (M+), 618, 522, 504, 414, 396

Nuclear magnetic resonance spectrum (270 MHz, $CDCl_3$, δ ppm): 0.93 (3H, triplet, J=7.3 Hz, CH—CH$_3$CH $_2$CH=$_2$CH—COO—) 4.02 (1H, doublet, J=13.3 Hz, $C_{26}H$) 4.86 (1H, doublet, J=13.3 Hz, $C_{26}H$) 7.01 (1H, triplet of doublets, J=6.9, 15.7H, $C_3H_7$—C$\underline{H}$=CH—COO—)

EXAMPLE 8

26-(4-Methyl-2-pentenoyloxy)milbemycin $A_4$
Compound No 8

Mass spectrum (EI Method, m/z): 654 (M+), 618, 522, 414, 396

Nuclear magnetic resonance spectrum (270 MHz, $CDCl_3$, δ ppm): 1.07 (6H, doublet, J=6.9 Hz, (CH$_3$)$_2$CH—CH=CH—COO—) 3.08 (1H, doublet of triplets, J=2.4, 9.3 Hz, $C_{25}H$) 4.72 (1H, doublet, J=13.3 Hz, $C_{26}H$) 4.86 (1H, doublet, J=13.3 Hz, $C_{26}H$) 6.99 (1H, doublet of doublets, J=6.5, 15.7 Hz, (CH$_3$)$_2$CH—C$\underline{H}$=CH—COO—)

EXAMPLE 9

26-(3-Hexenoyloxy)milbemycin $A_4$
Compound No 9

Mass spectrum (EI Method, m/z): 654 (M+), 414, 279, 195, 167

Nuclear magnetic resonance spectrum (270 MHz, $CDCl_3$, δ ppm): 3.07 (2H, doublet, J=6.4 Hz, CH—$_2$CH$_5$=CH—CH—CO$_2$O—) 4.68 (1H, doublet, J=12.9 Hz, $C_{26}H$) 4.79 (1H, doublet, J=12.9 Hz, $C_{26}H$)

EXAMPLE 10

26-(4-Pentenoyloxy)milbemycin $A_4$
Compound No 10

Mass spectrum (EI Method, m/z): 640 (M+), 604, 522, 264, 195, 167

Nuclear magnetic resonance spectrum (270 MHz, $CDCl_3$, δ ppm): 3.07 (1H, doublet of triplets, J=2.4, 9.3

Hz, $C_{25}H$) 4.69 (1H, doublet, J=13.7 Hz, $C_{26}H$) 4.79 (1H, doublet, J=13.7 Hz, $C_{26}H$) 4.99-5.10 (2H, multiplet, $\underline{CH_2}$=CH—$CH_2CH_2$—COO—)

EXAMPLE 11

26-Cinnamoyloxymilbemycin $A_4$
Compound No 11

Mass spectrum (EI Method, m/z): 688 (M+), 652, 522, 276, 195, 167

Nuclear magnetic resonance spectrum (270 MHz, $CDCl_3$, δ ppm): 3.07 (1H, doublet of triplets, J=2.4, 9.7 Hz, $C_{25}H$) 4.81 (1H, doublet, J=13.3 Hz, $C_{26}H$) 4.89 (1H, doublet, J=13.3 Hz, $C_{26}H$) 6.47 (1H, doublet, J=16.1 Hz, Ph—CH=$\underline{CH}$—COO—) 7.72 (1H, doublet, J=16.1 Hz, Ph—$\underline{CH}$=CH—COO—)

EXAMPLE 12

26-p-Chlorocinnamoyloxymilbemycin $A_4$
Compound No 12

Mass spectrum (EI Method, m/z): 722 (M+), 704, 540, 522, 504

Nuclear magnetic resonance spectrum (270 MHz, $CDCl_3$, δ ppm): 3.07 (1H, doublet of triplets, J=2.4, 8.9 Hz, $C_{25}H$) 4.81 (1H, doublet, J=13.3 Hz, $C_{26}H$) 4.93 (1H, doublet, J=13.3 Hz, $C_{26}H$) 6.44 (1H, doublet, J=16.1 Hz, p—Cl—Ph—CH=$\underline{CH}$—COO—) 7.67 (1H, doublet, J=16.1 Hz, p—Cl—Ph—$\underline{CH}$=CH—COO—)

EXAMPLE 13

5-O-Propionyl-2-(3-methyl-2-butenoyloxy)milbemycin $A_4$
Compound No 14

Mass spectrum (EI Method, m/z): 696 (M+), 604, 504, 414, 396, 356, 264, 195, 167, 151

Nuclear magnetic resonance spectrum (270 MHz, $CDCl_3$, δ ppm): 1.15 (3H, triplet, J=7.6 Hz, $CH_3CH_2CO$—) 2.40 (2H, quartet, J=7.6 Hz, $CH_3\underline{CH_2}CO$—) 3.07 (1H, broad triplet, J=8.0 Hz, $C_{25}H$) 4.11 (1H, doublet, J=6.0 Hz, $C_6H$) 4.50-4.76 (4H, multiplet, $C_{26}H$, $C_{27}H$) 5.65-5.95 (5H, multiplet, $C_3H$, $C_5H$, $C_9H$, $C_{10}H$, $(CH_3)_2C$=$\underline{CH}$—COO—)

EXAMPLE 14

5-O-Ethoxycarbonyl-2-(3-methyl-2-butenoyloxy)-milbemycin $A_4$
Compound No 15

Mass spectrum (EI Method, m/z): 712 (M+), 414, 396, 264, 195, 167, 151

Nuclear magnetic resonance spectrum (270 MHz, $CDCl_3$, δ ppm): 1.31 (3H, triplet, J=7.1 Hz, $CH_3CH_2OCOO$—) 3.07 (1H, doublet of triplets, J=2.4, 8.9 Hz, $C_{25}H$) 4.14 (1H, doublet, J=6.1 Hz, $C_6H$) 4.19 (2H, quartet, J=7.1 Hz, $CH_3\underline{CH_2}OCOO$—) 4.57-4.76 (4H, multiplet, $C_{26}H$, $C_{27}H$) 5.54 (1H, doublet of doublets, J=1.6, 6.1 Hz, $C_5H$)

EXAMPLE 15

26-(3-Methyl-2-butenoyloxy)ivermectin $B_{1a}$
Compound No 17

Mass spectrum (FAB Method, triethanolamine added, m/z): 1014, 992, 978, 962, 934, 878, 830, 299, 194

Nuclear magnetic resonance spectrum (270 MHz, $CDCl_3$, δ ppm): 3.07-3.29 (3H, multiplet, $C_4H$, $C_{4''}H$, $C_{25}H$) 3.35 (1H, singlet, $C_2H$) 3.48 (6H, singlet, two —$OCH_3$) 3.97 (1H, doublet, J=6.1 Hz, $C_6H$) 4.49 (1H, broad singlet, $C_5H$) 4.69 (2H, broad singlet, $C_{27}H$) 4.97 (1H, broad doublet, J=7.3 Hz, $C_{15}H$)

EXAMPLE 16

26-(3-Methyl-2-butenoyloxy) S-541A
Compound No 20

Mass spectrum (EI Method, m/z): 710 (M+), 592, 523, 468, 448, 423, 376

Nuclear magnetic resonance spectrum (270 MHz, $CDCl_3$, δ ppm): 3.75 (1H, doublet, J=10.9 Hz, $C_{25}H$) 4.67 (1H, doublet, J=13.3 Hz, $C_{26}H$) 4.82 (1H, doublet, J=13.3 Hz, $C_{26}H$) 5.20 (1H, doublet, J=8.9 Hz, $C_{32}H$)

EXAMPLE 17

Activity Tests: Adult Mites

Sample solutions were prepared each containing 0.3 ppm, 1 ppm or 3 ppm of individual compounds of this invention, or of one of three controls (milbemycin C, a mixture of milbemycin $C_1$ and milbemycin $C_2$ described in Japanese Patent, Laid Open 29742-84; 26-acetoxymilbemycin $A_4$; or 26-acetoxyavermectin $B_1a$), and 0.01% spreader.

Two-spotted spider mites (*Tetranychus urticae*) sensitive to organo-phosphorus insecticides were inoculated on the primary leaf of cowpea plants (*Vigna sinensis* Savi). One day after inoculation, 7 ml of the sample solution mentioned above was sprayed by a rotary sprayer (Mizuho Seisakusho Co) to give a sprayed amount of 3.5 mg/cm² of leaf. After being sprayed, the leaf was allowed to stand in a room kept at 25° C. After 3 days, whether the adult insects died or not was examined by a binocular microscope and the mortality (%) was calculated. The table below shows the results.

| compound number | mortality (%) | | |
|---|---|---|---|
| | 3 ppm | 1 ppm | 0.3 ppm |
| 1 ($\alpha_{11}$) | 100 | 100 | 93.0 |
| 2 ($\alpha_{13}$) | 100 | 95.6 | 77.3 |
| 3 ($\alpha_{14}$) | 100 | 100 | 100 |
| 5 | 100 | 100 | 54 |
| 6 | 100 | 100 | 55 |
| 7 | 100 | 100 | 61 |
| 8 | 100 | 100 | 51 |
| 9 | 100 | 100 | 50 |
| 10 | 100 | 100 | 44 |
| 11 | 100 | 100 | 40 |
| 12 | 100 | 100 | 55 |
| 14 | 100 | 100 | 65 |
| 15 | 100 | 100 | 60 |
| 16 | 100 | 100 | 57 |
| 17 | 100 | 100 | 53 |
| 20 | 100 | 100 | 59 |
| $C_1 + C_2$ | 100 | 100 | 28 |
| 26-acetoxymilbemycin $A_4$ | 92 | 81 | 23 |
| 26-acetoxyavermectin $B_{1a}$ | 83 | 65 | 15 |

EXAMPLE 18

Activity Tests: Mite Eggs

Sample solutions were prepared each containing 1 ppm or 3 ppm of individual compounds of this invention, or of one of three controls (milbemycin C, a mixture of milbemycin $C_1$ and milbemycin $C_2$ described in Japanese Patent, Laid Open 29742-84; 26-acetoxymilbemycin $A_4$; or 26-acetoxyavermectin $B_1a$), and 0.01% spreader.

Female adult two-spotted spider mites were allowed to lay eggs on the primary leaf of cowpea plants. The adult mites were removed to obtain test leaves each bearing about 50 eggs.

In a similar manner to that mentioned in the preceding Example, the sample solution was applied to the test leaf. After standing for 2 weeks in a room kept at 25° C., the number of unhatched eggs was counted, and the unhatched egg rates (%) were calculated.

The table below shows the results.

| compound number | ovicidal activity (%) | |
|---|---|---|
| | 3 ppm | 1 ppm |
| 1 ($a_{11}$) | 94 | 51 |
| 2 ($a_{13}$) | 94 | 71 |
| 3 ($a_{14}$) | 95 | 57 |
| 5 | 94 | 45 |
| 6 | 62 | 33 |
| 7 | 77 | 50 |
| 8 | 55 | 23 |
| 10 | 53 | 23 |
| 14 | 82 | 41 |
| 15 | 63 | 20 |
| 16 | 57 | 21 |
| 19 | 43 | 20 |
| $C_1 + C_2$ | 2.7 | 2.1 |
| 26-Acetoxymilbemycin $A_4$ | 31 | 12 |
| 26-Acetoxyavermectin $B_{1a}$ | 4.2 | 2.4 |

It was thus shown that the novel milbemycins of this invention showed a high acaricidal effect against adult mites at such a low concentration as 0.3 ppm, and also possessed useful ovicidal activity.

We claim:

1. A compound having the formula:

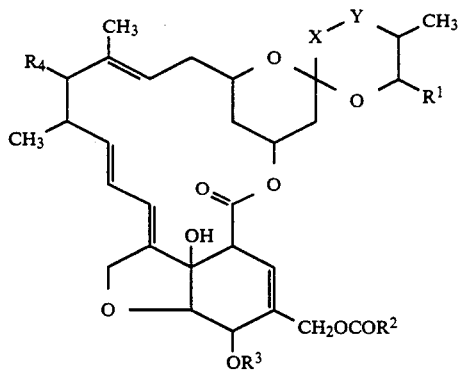

wherein:

—X—Y— is selected from the group consisting of —$CH_2$—$CH_2$—, —$CH_2$—CHOH—, —CH=CH—, and —$CH_2$—C(=O)—;

$R^1$ is selected from the group consisting of a methyl group, an ethyl group, an isopropyl group, a sec-butyl group and a group of formula —C($CH_3$)=CH$R^5$ in which $R^5$ is selected from the group consisting of a methyl group, an ethyl group and an isopropyl group;

$R^2$ represents a group of formula —($CH_2$)$_n$—C($R^6$)=C($R^7$)($R^8$) in which n is 0, 1 or 2, $R^6$ and $R^7$ each is selected from the group consisting of a hydrogen atom and a methyl group and $R^8$ is selected from the group consisting of a hydrogen atom, a $C_{1-4}$ alkyl group, a phenyl group and a phenyl group substituted with at least one substituent selected from the group consisting of halogen, methyl and nitro substituents;

$R^3$ is selected from the group consisting of a hydrogen atom, a methyl group, a hydroxy-protecting group, an ester-forming carboxylic acid residue, and an ester-forming carbonic acid residue; and $R^4$ is selected from the group consisting of a hydrogen atom and an α-L-oleandrosyl-α-L-oleandrosyloxy group, with the proviso that $R^4$ represents a hydrogen atom when the group $R^1$ is selected from the group consisting of a methyl group, an ethyl group, and groups of formula —C($CH_3$)=CH$R^5$ in which $R^5$ is selected from the group consisting of a methyl group, an ethyl group and an isopropyl group.

2. The compound of claim 1, wherein —X—Y— is selected from the group consisting of —$CH_2$—$CH_2$—, —$CH_2$—CHOH—, and —$CH_2$—C(=O)—.

3. The compound of claim 1, wherein $R^1$ is selected from the group consisting of a methyl group, an ethyl group and an isopropyl group, and $R^4$ is a hydrogen atom.

4. The compound of claim 1, wherein $R^1$ is selected from the group consisting of an isopropyl group and a sec-butyl group, and $R^4$ is an α-L-oleandrosyl-α-L-oleandrosyloxy group.

5. The compound of claim 1, wherein $R^1$ is a group of formula —C($CH_3$)=CH$R^5$ (in which $R^5$ is as defined in claim 1), and $R^4$ is a hydrogen atom.

6. The compound of claim 1, wherein $R^2$ is selected from the group consisting of groups of formula —CH=C($CH_3$)($R^{10}$), wherein $R^{10}$ is selected from the group consisting of a methyl group and an ethyl group.

7. The compound of claim 1, wherein $R^3$ is selected from the group consisting of a hydrogen atom, a lower alkanoyl group having from 1 to 4 carbon atoms, and a lower alkoxycarbonyl group having from 2 to 5 carbon atoms.

8. The compound of claim 1, wherein —X—Y— is —$CH_2$—$CH_2$—, $R^1$ is selected from the group consisting of a methyl group and an ethyl group, $R^2$ is a 2-methyl-1-propenyl group, and $R^3$ and $R^4$ are hydrogen atoms.

9. The compound of claim 1, which is selected from the group consisting of:
26-(3-Methyl-2-pentenoyloxy)milbemycin $A_4$;
26-(2-Butenoyloxy)milbemycin $A_4$;
26-(2-Methyl-2-butenoyloxy)milbemycin $A_4$;
26-(2-Hexenoyloxy)milbemycin $A_4$;
26-(4-Methyl-2-pentenoyloxy)milbemycin $A_4$;
26-(3-Hexenoyloxy)milbemycin $A_4$;
26-(4-Pentenoyloxy)milbemycin $A_4$;
26-Cinnamoyloxymilbemycin $A_4$;
26-p-Chlorocinnamoyloxymilbemycin $A_4$;
5-O-t-Butyldimethylsilyl-2-(3-methyl-2-butenyloxy)milbemycin $A_4$;
5-O-Propionyl-2-(3-methyl-2-butenoyloxy)milbemycin $A_4$;
5-O-Ethoxycarbonyl-2-(3-methyl-2-butenoyloxy)milbemycin $A_4$;
26-(3-Methyl-2-butenoyloxy)milbemycin D;
26-(3-Methyl-2-butenoyloxy)ivermectin $B_{1a}$;
26-(3-Methyl-2-butenoyloxy)avermectin $B_{1a}$;
23-Deoxy-26-(3-methyl-2-butenoyloxy) S-541A;
26-(3-Methyl-2-butenoyloxy) S541A; and
23-Keto-26-(3-methyl-2-butenoyloxy) S-541A.

10. The compound of claim 1, which is selected from the group consisting of:
26-(3-Methyl-2-pentenoyloxy)milbemycin $A_4$;
26-(2-Hexenoyloxy)milbemycin $A_4$;
26-(4-Methyl-2-pentenoyloxy)milbemycin $A_4$;
26-(4-Pentenoyloxy)milbemycin $A_4$;

26-Cinnamoyloxymilbemycin $A_4$;

5-O-Propionyl-2-(3-methyl-2-butenoyloxy)milbemycin $A_4$;

5-O-Ethoxycarbonyl-2-(3-methyl-2-butenoyloxy)milbemycin $A_4$;

26-(3-Methyl-2-butenoyloxy)milbemycin D;

26-(3-Methyl-2-butenoyloxy)ivermectin $B_{1a}$;

26-(3-Methyl-2-butenoyloxy)avermectin $B_{1a}$;

23-Deoxy-26-(3-methyl-2-butenoyloxy) S-541A;

26-(3-Methyl-2-butenoyloxy) S-541A; and

23-Keto-26-(3-methyl-2-butenoyloxy) S-541A.

11. The compound of claim 1, which is selected from the group consisting of:

26-(3-Methyl-2-pentenoyloxy)milbemycin $A_4$;

26-(3-Methyl-2-butenoyloxy)milbemycin D;

26-(3-Methyl-2-butenoyloxy)ivermectin $B_{1a}$;

26-(3-Methyl-2-butenoyloxy)avermectin $B_{1a}$;

23-Deoxy-26-(3-methyl-2-butenoyloxy) S-541A;

26-(3-Methyl-2-butenoyloxy) S-541A; and

23-Keto-26-(3-methyl-2-butenoyloxy) S-541A.

12. The compound of claim 1, wherein the compound is 26-(3-methyl-2-butenoyloxy)milbemycin $A_3$.

13. The compound of claim 1, wherein the compound is 26-(3-methyl-2-pentenoloxy)milbemycin $A_3$.

14. The compound of claim 1, wherein the compound is 26-(3-methyl-2-butenoyloxy)milbemycin $A_4$.

15. A parasiticidal composition which comprises a carrier and a parasiticidally effective amount of a compound of formula (I):

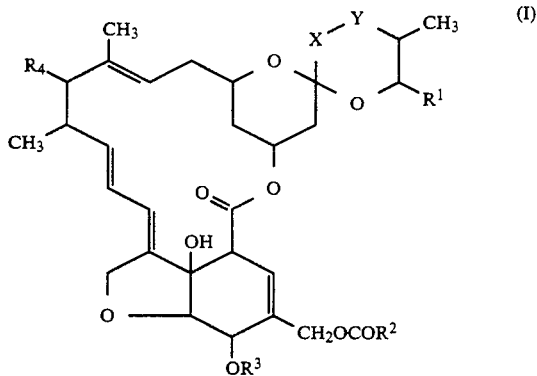

wherein:

—X—Y— is selected from the group consisting of —$CH_2$—$CH_2$—, —$CH_2$—CHOH—, —CH=CH—, and —$CH_2$—C(=O)—;

$R^1$ is selected from the group consisting of a methyl group, an ethyl group, an isopropyl group, a sec-butyl group and groups of formula —C($CH_3$)=$CHR^5$ in which $R^5$ is selected from the group consisting of a methyl group, an ethyl group and an isopropyl group;

$R^2$ represents a group of formula —($CH_2$)$_n$—C($R^6$)=C($R^7$)($R^8$) in which n is 0, 1 or 2, $R^6$ and $R^7$ each is selected from the group consisting of a hydrogen atom and a methyl group and $R^8$ is selected from the group consisting of a hydrogen atom, a $C_{1-4}$ alkyl group, a phenyl group and a phenyl group substituted with at least one substituent selected from the group consisting of halogen, methyl and nitro substituents;

$R^3$ is selected from the group consisting of a hydrogen atom, a methyl group, a hydroxy-protecting group, an ester-forming carboxylic acid residue, and an ester-forming carbonic acid residue; and $R^4$ is selected from the group consisting of a hydrogen atom and an α-L-oleandrosyl-α-L-oleandrosyloxy group, with the proviso that $R^4$ represents a hydrogen atom when the group $R^1$ is selected from the group consisting of a methyl group, an ethyl group, and groups of formula —C($CH_3$)=$CHR^5$ in which $R^5$ is selected from the group consisting of a methyl group, an ethyl group and an isopropyl group.

16. A method of treating or protecting animals or plants from the group consisting of damage by parasites selected from acarids, helminths and insects, which method comprises applying to said animals, to said plants or to seeds of said plants or to a locus including said animals, plants or seed an effective amount of a compound of formula (I):

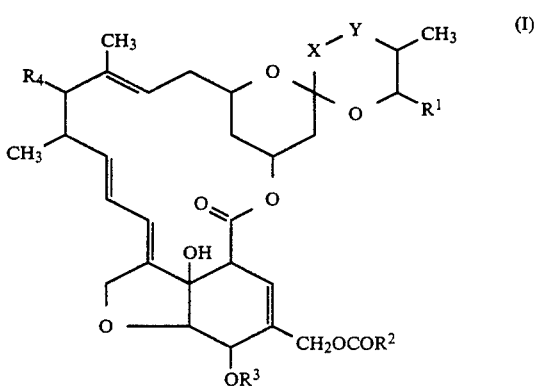

wherein:

—X—Y— is selected from the group consisting of —$CH_2$—$CH_2$—, —$CH_2$—CHOH—, —CH=CH—, and —$CH_2$—C(=O)—;

$R^1$ is selected from the group consisting of a methyl group, an ethyl group, an isopropyl group, a sec-butyl group and groups of formula —C($CH_3$)=$CHR^5$ in which $R^5$ is selected from the group consisting of a methyl group, an ethyl group and an isopropyl group;

$R^2$ represents a group of formula —($CH_2$)$_n$—C($R^6$)=C($R^7$)($R^8$) in which n is 0, 1 or 2, $R^6$ and $R^7$ each is selected from the group consisting of a hydrogen atom and a methyl group and $R^8$ is selected from the group consisting of a hydrogen atom, a $C_{1-4}$ alkyl group, a phenyl group and a phenyl group substituted with at least one substituent selected from the group consisting of halogen, methyl and nitro substituents;

$R^3$ is selected from the group consisting of a hydrogen atom, a methyl group, a hydroxy-protecting group, an ester-forming carboxylic acid residue, and an ester-forming carbonic acid residue; and $R^4$ is selected from the group consisting of a hydrogen atom and an α-L-oleandrosyl-α-L-oleandrosyloxy group, with the proviso that $R^4$ represents a hydrogen atom when the group $R^1$ is selected from the group consisting of a methyl group, an ethyl group, and groups of formula —C($CH_3$)=$CHR^5$ in which $R^5$ is selected from the group consisting of a methyl group, an ethyl group and an isopropyl group.

* * * * *